(12) United States Patent
Vlahakos

(10) Patent No.: US 6,613,356 B1
(45) Date of Patent: Sep. 2, 2003

(54) WEIGHT LOSS MEDICATION AND METHOD

(76) Inventor: Victor Vlahakos, 1740 W. 27th St., Houston, TX (US) 77008

( * ) Notice: Subject to any disclaimer, the term of this patent is extended or adjusted under 35 U.S.C. 154(b) by 0 days.

(21) Appl. No.: 09/685,713

(22) Filed: Oct. 10, 2000

(51) Int. Cl.$^7$ .................................................. A61K 9/20
(52) U.S. Cl. ........................ 424/464; 424/400; 424/451; 424/467; 424/489; 424/78.01
(58) Field of Search ................................. 424/400, 451, 424/464, 467, 489, 78.01

(56) References Cited

U.S. PATENT DOCUMENTS

| | | | |
|---|---|---|---|
| 4,497,798 A | | 2/1985 | Lambert |
| 4,771,074 A | | 9/1988 | Lammerant |
| 4,812,315 A | * | 3/1989 | Tarabishi .................... 206/828 |
| 4,843,093 A | | 6/1989 | Nagai |
| 5,292,774 A | | 3/1994 | Hiraide |
| 5,563,173 A | | 10/1996 | Yatsu |
| 5,858,365 A | | 1/1999 | Faller |
| 5,939,455 A | | 8/1999 | Rephaeli |
| 6,096,885 A | * | 8/2000 | Dezube et al. .............. 540/523 |

* cited by examiner

Primary Examiner—Thurman K. Page
Assistant Examiner—Charesse Evans
(74) Attorney, Agent, or Firm—Henry L. Smith, Jr.

(57) ABSTRACT

The invention involves a medication for weight loss by means of appetite suppression and a method for administering this medication to humans and other mammals. The medication comprises potassium butyrate or closely related chemical compounds, together with chemicals which facilitate the dispersion of the medication in the stomach.

19 Claims, No Drawings

WEIGHT LOSS MEDICATION AND METHOD

BACKGROUND FIELD OF INVENTION

The invention is a medication for weight loss in mammals through appetite suppression and a method for administering this medication.

BACKGROUND DESCRIPTION OF PRIOR ART

It is generally recognized in the medical profession that obesity among the populations of the United States and some other countries has been steadily increasing in the last several decades. Such obesity has caused or contributed to marked increases in the occurrence of heart disease, hypertension, diabetes, osteoarthritis of the knees and hips, and increased morbidity resulting from related medical conditions. It has been reported that 50% of all American adults are overweight. During the past five decades several medications have been tried with patients to reduce weight. Amphetamines acted on the brain by stimulating the release of norepinephrine and dopamine at the nerve synapses. This drug suffered from limited effectiveness and from side effects including nervousness, irritability, insomnia and potential for addiction. Other related compounds in this class of drugs include ephedrine, phenteramine, and phenylpropanolamine. While these medications have fewer side effects, they are approved by the FDA for use for only for three months at a time, a major disadvantage. Another medication, sibutramine (Meridia) also acts on the central nervous system but has as side effects headache, insomnia, chest palpitations, hypertension, and dry mouth. Another type of weight loss medication is orilistat (Xenecal), which acts by inhibiting the absorption of fat in the small intestine. This medication has as side effects oily stool, increased flatus, and occasional stool incontinence. Supplemental fat soluble vitamins (A, D, and E) must be given to avoid a deficiency of these vitamins caused by the medication. (Physician's Forum, March 2000, page 1 and 2; Harrison's Principles of Internal Medicine, 14th edition, page 456.)

Many methods and medications for weight reduction have been developed in the art. The following patents are representative of methods previously used.

U.S. Pat. No. 5,783,603, Jul. 21, 1998 to M. Majeed and V. Badmaev discloses a method of appetite suppression and weight loss by administering hydroxycitric acid in a form of a potassium salt extracted from Garcinia fruit. The patent also describes a method of increasing fat metabolism in the patient.

U.S. Pat. No. 4,497,798, Feb. 5, 1985 to T. C. Lambert discloses the administration of potassium compounds in liquid form to human beings to physiologically induce appetite suppression and appetite suppression response during times of hunger pains and for dampening the impulse to eat.

U.S. Pat. No. 4,843,093, Jul. 27, 1989 to Y. Nagai, T. Nakano, and Y. Oomura discloses various chemicals which are said to have an appetite regulating effect, including butyrolactone derivatives having the formula

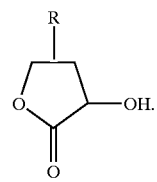

wherein R is a $C_4$–$C_{10}$ alkyl group.

The medications and methods of these patents, like many other patents, have as disadvantages, the fact that they involve chemicals which are either difficult to make, are not known to be naturally occurring in the body, or which may have unpleasant side effects for the patient.

SUMMARY OF INVENTION

The present invention comprises potassium butyrate and certain closely related chemical compounds, which reduce appetite in mammals when administered orally to the mammals. The invention also comprises certain other chemicals mixed with the butyrate compounds which facilitate the dispersion of the medication in the mammal's stomach, and it also involves a method both as to timing and dosage for administering the medication to humans. The invention is cheap, easy to manufacture, naturally occurring in mammals (and therefore is expected to have low toxicity) and may have other beneficial properties such as inhibited growth of certain cancers.

OBJECTS AND ADVANTAGES

The objects and advantages of the present invention are:
1. The medication is easy to manufacture.
2. The medication is inexpensive to manufacture.
3. The medication is a substance which often naturally occurs in the intestines of mammals, and is therefore expected to have minimal toxicity or side effects.
4. The medication adds to the physician's armamentarium against obesity.
5. There is a great body of literature about the substance's effects on humans, including beneficial effects such as promoting normal colonic epithelial growth while inhibiting cancerous growth (*Butyrate and the Colonocyte*, by Velazquez, Lederer and Rombeau, Digestive Diseases and Sciences, April, 1996).
6. The medication's dispersion in the mammal's stomach is facilitated by gas generating substances in the tablet or capsule.
7. The medication can be used for longer periods than many other weight loss medications.

Still further objects and advantages will become evident from the detailed description of the invention, and the drawings.

DESCRIPTION PREFERRED EMBODIMENT

The preferred embodiment of the invention involves the administration to mammals of the n-butyrate ion ($CH_3CH_2CH_2COO^-$). This butyrate ion comes from the potassium salt of butyric acid, specifically $K^+CH_3CH_2CH_2COO^-$. When this odorless alkaline salt is acidified below pH 7, the odiferous free acid butyric acid is liberated ($CH_3CH_2CH_2COOH$). Medical research indicates that the butyrate ion is actually beneficial to the colon epithelial cells, and they use it as a source of energy like the rest of the body uses glucose. It is also helpful in promoting healing after colon surgery, and it is thought to prevent the development of colon cancer.

OPERATION OF THE INVENTION

It is known that the presence of food in the stomach is associated with the presence of bacteria in the stomach. At least in the intestines, bacterial fermentation of food produces butyrate. Therefore ordinarily, the more food in the stomach, the more bacteria and, one would expect, the more butyrate present. The anorexic effect of the butyrate ion is thought to be due to the fact that its presence is a signal to the stomach receptors that there are bacteria in the stomach contents, which cause fermentation of the food. This situation would occur if the stomach contents were not being emptied promptly into the intestines. This occurs after a high-fat meal in which the stomach empties slowly into the small intestine. It also occurs in gastroenteritis, intestinal obstruction, and other nauseating conditions. Both the high-fat meal and the nauseating conditions have in common the fact that there are stagnant stomach contents of excess volume. Stagnation allows the normally sterile stomach interior to be colonized by bacteria migrating up from the lower small intestine. These bacteria ferment the food in the stomach, forming among other things, acetic acid, proprionic acid and butyric acid ($CH_3CH_2CH_2COOH$). Butyric acid has the distinctive smell of rancid butter or milk. The presence of exogenously administered butyric acid or butyrate ions apparently also causes stomach receptors to react as though there were stagnant food in the stomach, and causes the receptors to signal to the brain through the vagus nerve, thus suppressing the appetite. In effect, the stomach indicates to the brain that no more food is needed in the stomach, and that the stomach cannot handle what it already contains. Therefore, consuming the butyrate ion before each meal makes the stomach feel as if more was eaten than actually was eaten. The administration of butyrate ions appears to work best with high volume, low fat and low calorie foods, such as salads, thus making one feel as if the stomach contains high fat foods of equal volumes.

DOSAGES AND TESTS

The preferred starting dose is 50 mg of K butyrate or 264 mg of a 21% strength mixture in punctured capsules twice a day. The upper range of the preferred dose is about 1.15 grams of potassium butyrate or 5 of the size #0 filled capsules (described in this Application) taken three times a day, 1–25 minutes before meals, and taken with at least 8 ounces (240 cc) of water or other beverage. This is volunteer #2's present dose (discussed below), which seems to continue to be effective. One could reasonably increase the dose size to about 1.5 grams, but this dose has not been tested yet.

Taking a smaller dose, such as 690 mg or three of the size #0 filled capsules between meals with water or beverage in addition to the above 1.15 gram doses before meals is helpful when hunger returns between meals. Volunteer #2 has tested this and finds it useful on difficult days.

The maximum safe dose is probably 2.5 grams (2,500 mg) before meals. This is equal to 12 capsules of the present formulation. Taken with 360 cc or 12 ounces of beverage, the concentration in the lumen of the stomach would be 0.7%. The reason for choosing this limit is that instillation of butyric acid in a 1% concentration into mouse colons caused colitis. However in this study, alkaline butyrate ion in the same concentration did not cause colitis. By way of comparison, the physiologic concentration in the colon of butyrate is 10 mmoles/liter or 0.126% concentration. This is also equal to 453 mg (or about 2 capsules) diluted in 360 cc or 12 oz of beverage.

Rather than increasing the single dose amount before meals, adding doses between meals is probably safer. Butyrate is probably rapidly cleared within one or two hours from the stomach by gastric emptying. The half-life in the serum is only 2 minutes (U.S. Pat. No. 5,858,365, column 3). Therefore even 10 doses a day or 36 capsules would probably be well tolerated. This would probably be about the practical limit due to the number of capsules as well. It is not recommended to increase the concentration of butyrate in the powder mixture because of the risk of localized areas or "hot spots" of excess concentration of butyrate and KOH along the stomach wall.

Based on the inherent safety of butyrate as discussed in medical literature, experimental administration of butyrate was begun on two volunteers. Tests on the two human volunteers has produced weight loss of 17 pounds and 40 pounds respectively at a dosage of 3–5 capsules, once or twice daily (volunteer #1); or 3–5 capsules three times per day (volunteer #2). Each capsule contained approximately 140 mg of potassium butyrate at the start of the test period, and 231 mg each at the end of the test period. The butyrate capsules typically contain 231 to 287 mg of potassium butyrate and 345 to 431 mg of corn starch and 345 to 431 mg of sodium bicarbonate in a 920 to 1 100 mg Size 0 Lilly gelatin capsule. The potassium butyrate is prepared by oxidizing 1-butanol with potassium permanganate in aqueous solution at between 180° F. and 212° F. This reaction produces manganese dioxide and butyric acid and KOH. The manganese dioxide is quite insoluble and is filtered out, and the butyric acid is then neutralized by the potassium hydroxide formed, thus forming the salt, potassium butyrate. The following reactions are thought to produce the potassium butyrate:

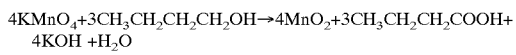

followed by

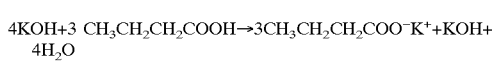

In a typical production run, 125 to 126 grams (0.8 moles) of potassium permanganate are reacted with an excess amount of butanol in the range of 90 to 120 ml (about 0.9–1.2 moles).

In a typical production run, 125 to 126 grams of potassium permanganate are dissolved in 5 to 6 liters of distilled water to make a saturated solution. This is divided for safety considerations among 10–14 glass bottles containing 430–500 cc each. These are heated in a pot of salted water boiling at 216° F. (102.2° C.) in a double boiler fashion. Once the permanganate solution reaches 83° C. or 180° F., in about 10 minutes, addition of aliquots of butanol is begun. 2 cc of butanol are added to each of the bottles every 10 minutes for the first two additions, and every 5 minutes for the last two additions, stirring well each time. A total of 8 to 10 cc of butanol is used per bottle. This is an excess amount of butanol to ensure that all the permanganate is used up (reduced).

The solution should change from a royal purple solution to a deep brown suspension. This is filtered through standard paper coffee filters. The brown manganese dioxide is filtered out leaving a clear colorless solution of potassium butyrate $K^+CH_3CH_2CH_2COO^-$ plus KOH produced by the reaction at the quantity of ⅓ mole of KOH for every one mole of potassium butyrate produced. Also, excess butanol is present in the solution. This solution is desiccated at a temperature not to exceed 212° F.(100° C.). A dry white powder is formed. Brownish discoloration of the powder indicates overheating has occurred and that the batch must be discarded. Desiccation of the solution would be more reliably done with less chance of overheating if done in a vacuum chamber. The actual yield of this method is about ½ of the predicted amount—about 35–40 grams of potassium butyrate for each 125 grams of potassium permanganate used. This is due to loss of permanganate-produced oxygen, escaping from the heated solution. One part of the resultant powder, a mixture of potassium butyrate with a small amount of KOH as noted above, is mixed with 1½ parts by weight of corn starch. This mixture is quite alkaline. To partially neutralize this powder, it is spread in a thin layer on a plate or other surface, and ¹⁄₁₀th strength sulfuric acid ($H_2SO_4$) is dripped onto this in an even fashion using a micropipette. A proportion of 2 cc is used for every 25 grams of desiccated K butyrate(+KOH) powder.

The powder is remixed, and lumps are broken up. Then 1½ parts by weight of sodium bicarbonate is added. The resultant 100 grams of powder consists of approximately 21% potassium butyrate, 3.75% KOH. One third of the latter is neutralized with the $H_2SO_4$. Because this powder is still alkaline, little or no volatile free butyric acid is present so the powder is odorless and tasteless.

This mixture is stuffed into #0 Lilly brand empty gelatin capsules. These were obtained from the Eli Lilly company, Indianapolis, Ind., 46285. When filled, the capsules are 25–27 mm long and 8 mm in diameter. Each capsule contains up to 1100 mg of powder and therefore approximately 231 mg of potassium butyrate each. These filled reassembled capsules have 14 1 mm holes, 7 on each side, produced by hypodermic needles. These holes could be anywhere from 0.5 to 1.5 mm, and 10–20 in number. Too many or too large holes cause the capsule to crack, and too few or too small holes prevent the powder from dispersing fast enough. A manually powered device was constructed and used to puncture the capsules at 3 at a time.

The purpose of the puncture holes in the capsules is to disperse the potassium butyrate rapidly and widely in the stomach. Therefore, no one area of stomach mucosal lining would be exposed to an inordinate concentration of butyrate ion. The purpose of the sodium bicarbonate in the mixture is to facilitate the dispersion of this medication. This is done by the production of $CO_2$ inside the capsule which provides the motive force to eject the medication through the puncture holes. The $CO_2$ is produced when stomach liquids of the mammal enter the capsule through some of the holes in the capsule. These gastric fluids usually have an acid pH of 2–5 due to HCl secreted by the parietal cells in the stomach wall. When this HCl combines with the $NaHCO_3$ in the capsule, $CO_2$ is formed. (+$H_2O$ and NaC). Other means for producing $CO_2$ include but are not limited to potassium carbonate, magnesium carbonate and similar carbonates and bicarbonates. Also possible is use of other commonly used inert ingredients such as talc and magnesium stearate in the compounding of this drug, and in fact by using these the resulting mixture could be pressed into a tablet. This tablet could be coated with a gelatin coating thus saving the 3 cent cost of the empty gelatin capsule. With further developments, puncture holes could also be made in this gelatin tablet as well. This would accomplish the goal of rapid, even dispersion of butyrate in the stomach as well as the present form (embodiment) of the invention.

The butyrate itself could be made more economically by an older method of producing it, known to those skilled in the art of using fermentation. The bacteria, bacillus subtilus, is introduced into starch or sugar, and the fermentation process begins. Calcium carbonate is added to neutralize the acidity of the butyric acid produced, and therefore to increase the yield. The calcium butyrate formed is soluble in cold water, and this fact probably facilitates the separation of this product from the fermentation mixture.

The punctured capsules containing the potassium butyrate are fairly odorless. However, when they contact the acid environment of the stomach, (or even skin surface) the volatile butyric acid is produced with the distinctive sour stomach odor or vomitious odor. The capsules are typically administered to a patient 10 to 20 minutes before each meal with 8 oz of water, and the typical dosage is 3–4 of the 230 to 287 ml capsules of potassium butyrate. This is the best mode of using the invention discovered to date.

ADDITIONAL EMBODIMENTS

It is believed that chemical compounds closely related to potassium butyrate would have a similar appetite suppressing effect in the stomach of mammals because of the reaction described above in which the stomach receptors erroneously sense that the stomach is full of food which has been slow to digest, and therefore hunger sensations are suppressed. It is predicted based on general chemical principles, that butyric acid, isobutyric acid, betahydroxybutyric acid and alphahydroxybutyric acid as well as their sodium, calcium, magnesium and potassium salts would each have appetite suppressing effects, although these were not tested. Sodium bicarbonate, calcium carbonate or any other pharmaceutically acceptable chemical means for generating carbon dioxide or other pharmaceutically acceptable gas on contact with the mammal's stomach liquids, can be incorporated into the tablet or capsule to facilitate dispersion of the medication in the mammal's stomach. These other compounds containing the butyrate ion or having a structure similar to potassium butyrate or butyric acid may also be effective in appetite suppression, and are within the scope of the present invention.

In humans, dosage of medications is often adjusted on the basis of body surface area. The body surface area of an average adult is 1.6 square meters. Dosages of possible mixtures of butyrate derivatives discussed in the paragraph above should be adjusted so that the dosage of the sodium, calcium, magnesium and potassium ions do not exceed the recommended daily allowances (RDA) for humans.

ALTERNATIVE EMBODIMENTS

The butyric acid-related compounds might also be administered to mammals orally with constituents other than corn starch and sodium bicarbonate, which may have different effects on the rapidity at which the capsules dissolve and are absorbed by the stomach. Other ranges of dosage of potassium butyrate and frequency of administration to mammals might be used.

TEST DATA

The following data on two human volunteers and tests on mice illustrate the effectiveness of the invention.

The inventor, after having been convinced by the medical literature of the inherent safety of butyrate in humans, began experimental administration of potassium butyrate as a weight loss agent to two volunteers, one of which was himself. The starting dose was 23 mg twice a day, in capsules containing 230 mg of a 10% mixture each. Volunteer #1's starting weight then was 185 lb measured in the morning, fasting. Volunteer #1's height was 5'6" making his body mass index (BMI) 27. Note this is in the range regarded as being overweight (25–30). The dose was increased to 66 mg twice a day a couple of days later, and after 20 days the weight declined to 181 lb. The dose was increased to 130 mg twice a day before meals after about a month. Weight after 2 months was 174 lb. During the $4^{th}$ through $7^{th}$ month, the dose averaged 280 mg twice a day on about half the days, skipping it on alternate days. Weight reached its lowest point after about 7 months: 168 lb, BMI 24.5, which is the upper range of normal. After that, the dose has been an average of 660 mg once a day, taken before meals, but only used on alternate days. The weight on this low dose rose to 174 lb and has stayed within 4 lb of that for the last 5 months.

Prior to starting K butyrate, volunteer #1 had a hypertension requiring 4 mg per day of Cardura (Doxozocin) and had bilateral carpal tunnel syndrome symptoms as well as electromyogram (EMG) findings diagnostic for this. After about 14 months the carpal tunnel syndrome symptoms improved markedly, and the blood pressure was normal without medication. No adverse effects occurred except for occasional transient epigastric aching soon after a dose, but this has been quite rare and usually occurs if capsules are not taken with adequate water, and when not taken before a meal. No halitosis or foul eructation occurred. The blood counts and survey chemistries (SMA-18 or comprehensive chemistry) checked periodically have been normal. Particularly, the liver enzymes and liver function tests have remained normal. Triglyceride values were initially elevated at 310 but declined to 230 after about 6 months. However, the cholesterol and cholesterol ratios have not changed significantly. Over 4 months total cholesterol changed from 235, HDL ("good cholesterol") 48, to total cholesterol 236, HDL cholesterol 47.

Another test subject, volunteer #2, started on potassium butyrate when weight was 256 lb, height 5'3", BMI 40. Prior to this use of butyrate, subject's most successful weight losses was 50 lb over a 3 month period while on Optifast program, a 400 calorie a day supplemented fasting program.

The starting dose of butyrate was 40 mg three times a day. It was rapidly escalated to 560 mg before each meal and continued on that dose for about 6 months, when the dose was increased to 800 mg three times a day. Weight after 6 months was 222 lbs. The same dose was continued from that point for another 6 months. Then her weight was 220. Dose was then increased to 1150 mg three times a day for another 8 days. Then her weight was 216 after about a year, for a total of 40 lbs of weight loss during this slightly more than one year duration clinical trial. BMI declined to 35. During butyrate use no abnormalities have appeared on periodic comprehensive chemistry blood tests nor on blood counts.

Several chronic medical conditions have improved since Volunteer #2 has been on butyrate: (1) Exercise tolerance has almost doubled as measured on treadmill exercise stress tests. During previous stress test she was able to walk 4 minutes on the treadmill before too fatigued to go further. During a stress test after 1 year's use of butyrate she was able to walk 7 minutes. Both of these tests were stress thallium tests where the standard stress test is enhanced by nuclear imaging scans and the results were normal in both cases. Both were done because of several days of chest pains which were found not to be cardiac in origin and which resolved in a few days. (2) Hypercholesterolemia and hypertriglyceridemia have improved. Total cholesterol dropped from 266, HDL ("good cholesterol") 56, LDL("bad cholesterol")160, and triglycerides 269 to readings of total cholesterol 238, HDL 52, LDL 150, and triglycerides 179. (3) Fatigue has lessened and feeling of general well being has improved.

Two mouse experiments involved 8 adolescent common white mice, still in the growth period. Four were assigned to the butyrate group and were fed K butyrate mixed in pieces of chocolate 300–400 mg size twice a day, and the other four mice were assigned to the non-butyrate group and were fed the same size pieces of plain chocolate. Both groups of mice were otherwise cared for in an identical fashion and fed twice as many food pellets as recommended. The dose of butyrate initially chosen was 3.47 mg per dose scaled down from the human dose according to the ratio of body surface area of mouse compared to man. This was estimated at 1:250. Because this was well tolerated, the dose was increased to 11.5 mg twice a day after about one month.

During the 10 week experiment, the 2 non-butyrate mice gained an average of 18.6 grams each and the 2 butyrate mice gained an average of 17 grams each or about 10% less.

There has been no difference in the behavior, activity or agility between the butyrate group and the non-butyrate group of mice.

Another test on adult mice was run for about 9 weeks. Butyrate was mixed with chocolate and/or cornstarch and the mixture was added to the mice's food (a commercial guinea pig food—Aytec Supreme Daily Blend Guinea Pig Diet). The butyrate dose started at 11.1 mg per mouse twice a day at the beginning of the study and ended up at 58 mg per mouse twice a day at the end of the study. The non-butyrate-fed mice had the same chocolate and/or cornstarch added to their food in equal weight compared to the butyrate-fed mice. The four butyrate mice gained an average of 50 mg each over the 67 day test period, and the four non-butyrate mice gained an average of 325 mg each over the 67 day test period. While no weight loss occurred in either group the butyrate mice gained less weight, by a ratio of about 6.5 to 1.

CONCLUSION, RAMIFICATIONS, AND SCOPE

A number of changes are possible to the chemicals and methods described above, while still remaining within the scope and spirit of the invention. Many variations are possible in the butyrate ion, including branched chain molecules and various single radicals substituted for hydrogen atoms in the butyrate chain. The pharmaceutically acceptable variation on butyric acid can be administrated to mammals in a wide range of dosages and frequency of administration including before meals or in other aliquot dosages throughout the day. The butyric acid derivative can be administered by itself or mixed with calcium carbonate, sodium bicarbonate or similar compounds which react with stomach liquids to speed dissolution of the capsule or tablet. Gelatin or other capsules or tablets can be used to administer the butyrate. The capsules or tablets can have varying number of puncture holes or holes formed by other methods to facilitate the breakup of the tablets or capsules in the stomach.

The specifics about the form of the invention described in this application are not intended to be limiting in scope. The scope of the invention is to be determined by the Claims, and their legal equivalents, not the examples given above.

I claim:

1. A process for causing weight loss, or avoidance of weight gain, in mammals, comprising oral administration to said mammals of butyric acid or one or more pharmaceutically effective and acceptable salts or derivatives of butyric acid selected from the group consisting of/butyric acid, sodium butyrate, calcium butyrate, potassium butyrate, magnesium butyrate, alphahydroxybutyric acid, sodium alphahydroxybutyrate, calcium alphahydroxybutyrate, potassium alphahydroxybutyrate, magnesium alphahydroxybutyrate, betahydroxybutyric acid, sodium betahydroxybutyrate, calcium betahydroxybutyrate, potassium betahydroxybutyrate, magnesium betahydroxybutyrate, isobutyric acid, sodium isobutryate, calcium isobutyrate, potassium isobutyrate, and magnesium isobutyrate.

2. The process of claim 1, wherein said salts or derivatives are administered orally to said mammal in a dissolvable tablet or capsule.

3. The process of claim 2, wherein the contents of said capsule or tablet further comprise sodium bicarbonate, calcium carbonate, or potassium bicarbonate for producing carbon dioxide gas on contact with the stomach liquids of said mammal wherein the amount of sodium bicarbonate, calcium carbonate or potassium bicarbonate is sufficient to cause the breakup of the capsule or tablet thus releasing the salts or derivatives, but insufficient to cause distension of the stomach of the mammal.

4. The process of claim 3, wherein said capsule or tablet contains a plurality of holes, whereby stomach liquids of the mammal can more quickly enter the capsule, thereby reacting with the sodium bicarbonate, the calcium carbonate or potassium bicarbonate producing means to produce carbon dioxide gas which facilitates breakup of said capsule, thus speeding the release of the contents of said capsule into the stomach.

5. The process of claim 1, wherein the total amount of said butyric acid, alphahydroxybutyric acid, betahydroxybutyric acid, isobutyric acid, or their sodium, potassium, calcium, or magnesium salts administered to a human being is at least 60 milligrams per square meter of body surface area per day.

6. The process of claim 1, wherein the total amount of said butyric acid, alphahydroxybutyric acid, betahydroxybutyric acid, isobutyric acid, or their sodium, potassium, calcium, or magnesium salts administered to a human being is between 60 milligrams and 900 milligrams per square meter of body surface area per day, inclusive.

7. The process of claim 1, wherein the total amount of said butyric acid, alphahydroxybutyric acid, betahydroxybutyric acid, isobutyric acid, or their sodium, potassium, calcium, or magnesium salts administered to said mammal is greater than 0.9 grams, and equal to or less than 4.7 grams, per square meter of body surface area per day for all salts or derivatives, except for magnesium salts, wherein the upper limit for magnesium salts is 2.35 grams per square meter of body surface per day.

8. The process of claim 5, wherein the total daily amount of said butyric acid or derivative or salt is divided into 3 substantially equal doses, each administered orally to said mammal before each of three meals per day.

9. The process of claim 6, wherein the total daily amount of said butyric acid or derivative or salt is divided into 3 substantially equal doses, each administered orally to said mammal before each of three meals per day.

10. The process of claim 7, wherein the total daily amount of said butyric acid or derivative or salt is divided into 3 substantially equal doses, each administered orally to said mammal before each of three meals per day.

11. The process of claim 5, wherein the daily dose of said butyric acid or derivative or salt is divided into a plurality of doses up to and including 10 per day.

12. The process of claim 6, wherein the daily dose of said butyric acid or derivative or salt is divided into a plurality of doses up to and including 10 per day.

13. The process of claim 7, wherein the daily dose of said butyric acid or derivative or salt is divided into a plurality of doses up to and including 10 per day.

14. A composition of matter comprising a capsule capable of dissolving in the stomach of a mammal, wherein said capsule contains, in an amount effective for weight loss or avoidance of weight gain in said mammal, one or more of the compounds selected from the group consisting of/butyric acid, sodium butyrate, calcium butyrate, potassium butyrate, magnesium butyrate, alphahydroxybutyric acid, sodium alphahydroxybutyrate, calcium alphahydroxybutyrate, potassium alphahydroxybutyrate, magnesium alphahydroxybutyrate, betahydroxybutyric acid, sodium betahydroxybutyrate, calcium betahydroxybutyrate, potassium betahydroxybutyrate, magnesium betahydroxybutyrate, isobutyric acid, sodium isobutryate, calcium isobutyrate, potassium isobutyrate, and magnesium isobutyrate.

15. The composition of matter in claim 14, wherein the contents of the capsule further comprise sodium bicarbonate, calcium carbonate or potassium bicarbonate for producing carbon dioxide gas on contact with the stomach liquids of said mammal wherein the amount of sodium bicarbonate, calcium carbonate or potassium bicarbonate is sufficient to cause the breakup of the capsule or tablet thus releasing the salts or derivatives, but insufficient to cause distension of the stomach of the mammal.

16. The composition of matter of claim 15, wherein said capsule has a plurality of holes, whereby said mammal's stomach liquids can more rapidly enter the capsule and facilitate its breakup in said mammal's stomach.

17. A composition of matter comprising a tablet capable of dissolving in the stomach of a mammal, wherein said tablet contains, in an amount effective for weight loss or avoidance of weight gain in said mammal, one or more of the compounds selected from the group consisting of/butyric acid, sodium butyrate, calcium butyrate, potassium butyrate, magnesium butyrate, alphahydroxybutyric acid, sodium alphahydroxybutyrate, calcium alphahydrokybutyrate, potassium alphahydroxybutyrate, magnesium alphahydroxybutyrate, betahydroxybutyric acid, sodium betahydroxybutyrate, calcium betahydroxybutyrate, potassium betahydroxybutyrate, magnesium betahydroxybutyrate, isobutyric acid, sodium isobutryate, calcium isobutyrate, potassium isobutyrate, and magnesium isobutyrate.

18. The composition of matter of claim 17, wherein the contents of said tablet further comprise sodium bicarbonate, calcium carbonate or potassium bicarbonate for producing carbon dioxide gas on contact with the stomach liquids of said mammal wherein the amount of sodium bicarbonate, calcium carbonate or potassium bicarbonate is sufficient to cause the breakup of the capsule or tablet thus releasing the salts or derivatives, but insufficient to cause distension of the stomach of the mammal.

19. The composition of matter of claim 18, wherein said tablet has a plurality of holes, whereby said mammal's stomach liquids can more rapidly enter the capsule and facilitate its breakup in said mammal's stomach.

* * * * *

(12) INTER PARTES REVIEW CERTIFICATE (2328th)
United States Patent
Vlahakos

(10) Number: US 6,613,356 K1
(45) Certificate Issued: Sep. 2, 2021

(54) WEIGHT LOSS MEDICATION AND METHOD

(75) Inventor: Victor Vlahakos

(73) Assignee: AXCESS GLOBAL SCIENCES, LLC

Trial Number:

IPR2019-01141 filed Jun. 3, 2019

Inter Partes Review Certificate for:

Patent No.: 6,613,356
Issued: Sep. 2, 2003
Appl. No.: 09/685,713
Filed: Oct. 10, 2000

The results of IPR2019-01141 are reflected in this inter partes review certificate under 35 U.S.C. 318(b).

INTER PARTES REVIEW CERTIFICATE
U.S. Patent 6,613,356 K1
Trial No. IPR2019-01141
Certificate Issued Sep. 2, 2021

AS A RESULT OF THE INTER PARTES REVIEW PROCEEDING, IT HAS BEEN DETERMINED THAT:

Claims 3, 4, 6, 7, 9, 10, 12, 13, 15, 16, 18 and 19 are found patentable.

Claims 1, 2, 5, 8, 11, 14 and 17 are cancelled.

\* \* \* \* \*